United States Patent
Berlich et al.

(10) Patent No.: US 10,076,531 B2
(45) Date of Patent: Sep. 18, 2018

(54) DIALYSIS SOLUTION, USE OF A DIALYSIS SOLUTION AND CHEMICAL COMPOUND

(71) Applicant: Fresenius Medical Care Deutschland GmbH, St. Wendel (DE)

(72) Inventors: Robert Berlich, St. Wendel (DE); Thomas Schweitzer, St. Wendel (DE); Lisa Finkler, Nonnweiler (DE); Thomas Heinze, Jena (DE); Robert Hampe, Rudolstadt (DE)

(73) Assignee: Fresenius Medical Care Deutschland GmbH, St. Wendel (DE)

( * ) Notice: Subject to any disclaimer, the term of this patent is extended or adjusted under 35 U.S.C. 154(b) by 0 days.

(21) Appl. No.: 15/175,384

(22) Filed: Jun. 7, 2016

(65) Prior Publication Data

US 2016/0367574 A1   Dec. 22, 2016

(30) Foreign Application Priority Data

Jun. 16, 2015   (DE) .......................... 10 2015 007 626

(51) Int. Cl.

| | |
|---|---|
| *A61K 31/718* | (2006.01) |
| *A61M 1/28* | (2006.01) |
| *A61K 31/662* | (2006.01) |
| *A61K 33/00* | (2006.01) |
| *C08B 31/06* | (2006.01) |
| *C08L 3/06* | (2006.01) |
| *A61M 1/16* | (2006.01) |

(52) U.S. Cl.
CPC .......... *A61K 31/662* (2013.01); *A61K 31/718* (2013.01); *A61K 33/00* (2013.01); *A61M 1/287* (2013.01); *C08B 31/066* (2013.01); *C08L 3/06* (2013.01); *A61M 1/1654* (2013.01)

(58) Field of Classification Search
None
See application file for complete search history.

(56) References Cited

U.S. PATENT DOCUMENTS

| | | | |
|---|---|---|---|
| 3,553,194 A | 1/1971 | Verbanac et al. | |
| 4,002,730 A * | 1/1977 | Hartman | A61K 51/02 424/1.37 |
| 6,248,726 B1 | 6/2001 | Alsop et al. | |
| 2004/0014961 A1 | 1/2004 | Backer et al. | |
| 2013/0056678 A1 | 3/2013 | Fenn et al. | |

OTHER PUBLICATIONS

International Search Report and Written Opinion issued in corresponding International Patent Application No. PCT/EP2016/000999 dated Aug. 10, 2016 (with English translation of International Search Report) (15 pages).
Feiga et al., "Note on the Reaction of Corn Starch with Chloromethylphosphonic Dichloride in Pyridine," Cereal Chemistry, 1967, vol. 44, No. 5, pp. 554-557.
Heinze et al., "Simple synthesis of mixed cellulose acylate phosphonates applying n-propyl phosphonic acid anhydride," Cellulose, 2012, vol. 19, pp. 523-531.
German Search Report issued in corresponding German Patent Application No. 10 2015 007 626.4 dated Jan. 11, 2016 (5 pages).

\* cited by examiner

*Primary Examiner* — Robert T. Crow
*Assistant Examiner* — John P Nguyen
(74) *Attorney, Agent, or Firm* — Kilyk & Bowersox, P.L.L.C.

(57) ABSTRACT

The present invention relates to a dialysis solution having at least one osmotic agent, wherein the osmotic agent is starch propylphosphonate.

15 Claims, 11 Drawing Sheets

DIALYSIS SOLUTION, USE OF A DIALYSIS SOLUTION AND CHEMICAL COMPOUND

Figure 1:
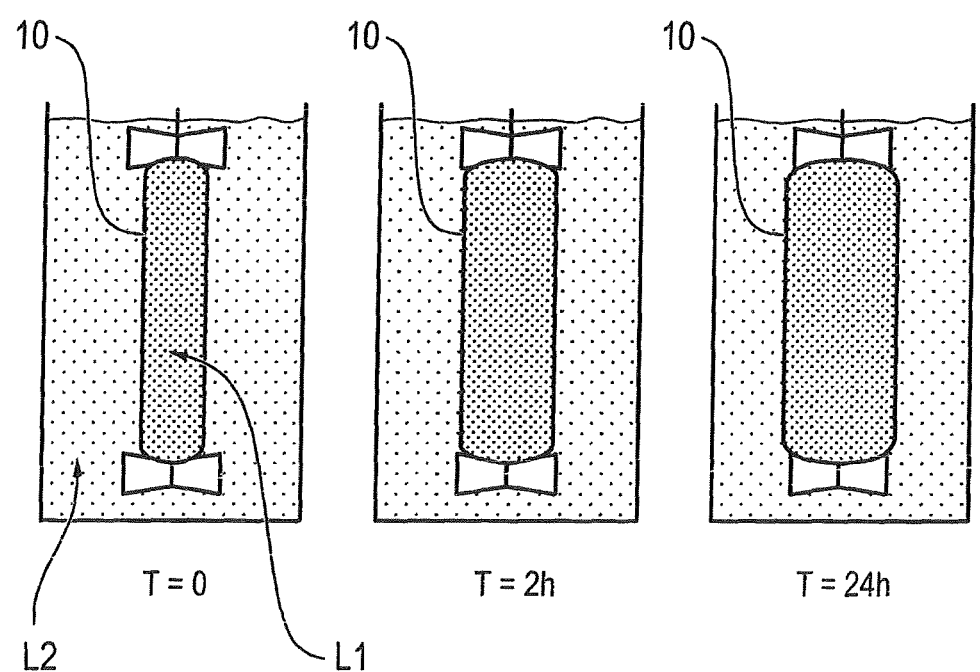

The present invention relates to a dialysis solution having at least one osmotic agent.

Dialysis solutions such as are used in peritoneal dialysis, hemodialysis, hemodiafiltration, etc. are known in a number of different compositions.

DE 10 2004 023 828 A1, for example, discloses a solution for a peritoneal dialysis which contains, in addition to electrolytes, an osmotic agent in the form of glucose.

The glucose serving as an osmotic agent has the result that the transport of water via the membrane is accelerated and that the ultrafiltration rate is thus improved. A further known osmotic agent is icodextrin which is a starch-derived branched glucose polymer.

It is the underlying object of the present invention to further develop a dialysis solution such that its ultrafiltration performance is increased with respect to known dialysis solutions.

This object is achieved by a dialysis solution having the features of claim 1. Provision is accordingly made that the osmotic agent is starch propylphosphonate. Starch propylphosphonates are produced, for example, by reacting starch with propylphosphonic acid anhydride, however, the invention is not restricted to this method of synthesis of starch propylphosphonates.

It has surprisingly been found that starch propylphosphonates have a very high efficacy in use as osmotic agents.

Provision is made in an embodiment of the invention that the dialysis solution contains exactly one kind or also a plurality of kinds of different starch propylphosphonates. This plurality of kinds of starch propylphosphonates can differ, for example, in the average degree of substitution and/or also in the molecular mass and/or in the reactant from which they are produced.

Provision is made in a further embodiment of the invention that the dialysis solution does not contain any further osmotic agents except for starch propylphosphonate.

Embodiments are, however, also covered by the invention in which one or more further osmotic agents such as glucose and/or icodextrin are present in addition to starch propylphosphonate.

The starch propylphosphonate of the dialysis solution in accordance with the invention is preferably water-soluble.

The average degree of substitution of the starch propylphosphonate of the dialysis solution in accordance with the invention preferably lies in the range from 0.1 to 1.2.

The term "degree of substitution" is understood within the framework of the present invention as the mean number of substituents per anhydroglucose unit of the starch. The degree of substitution can adopt values between 0 and 3.

A range of the average degree of substitution is preferably in the range from 0.2 to 0.5.

The starch propylphosphonate of the dialysis solution in accordance with the invention is preferably produced by conversion of polysaccharides, in particular of starch and preferably of depleted starch. In this respect, the polysaccharides, in particular the starch, preferably have a number average molar mass Mn in the range 3000 g/mol-5000 g/mol.

The dialysis solution preferably contains electrolytes as well as at least one buffer in addition to the osmotic agent or agents.

The electrolytes can be ions of sodium and/or potassium and/or calcium and/or magnesium. Chloride is preferably contained as the anion.

The buffer or buffers can comprise lactate ions and/or hydrogen carbonate ions. The buffer serves the setting of a physiological pH. The pH of the dialysis solution is preferably in the range from 6.8 to 7.2.

The dialysis solution in accordance with the invention can be used, for example, in hemodialysis, in hemodiafiltration or also in peritoneal dialysis.

The present invention furthermore relates to the use of a dialysis solution in accordance with one of the claims 1 to 12 for a blood treatment process.

As stated, the blood treatment process can be hemodialysis or also hemodiafiltration.

The use of the dialysis solution in accordance with the invention in peritoneal dialysis is also conceivable and covered by the invention.

The starch propylphosphonate used in the dialysis solution in accordance with the invention is preferably produced from one or more polysaccharides and in particular from starch in accordance with a process known per se. In this respect, polysaccharides, in particular starch having different molecular masses, and in particular having comparatively low molecular masses in the range of 3000 g/mol to 5000 g/mol can be used.

The preferably completely water-soluble starch propylphosphonates in accordance with the invention preferably have an average degree of substitution (DS) in the range from 0.1 to 1.2, and in particular in the range from 0.2 to 0.5.

As can be seen from the embodiments shown in the following, starch propylphosphonates demonstrate exceptional efficacy when used as osmotic agents.

The present invention furthermore relates to the substance starch propylphosphonate itself or to a substance mixture containing starch propylphosphonate. The starch propylphosphonate can in this respect be configured in accordance with one or more of the features disclosed within the framework of the invention.

The starch propylphosphonate is preferably completely water-soluble.

The average degree of substitution of the starch propylphosphonate can thus preferably lie in the range from 0.1 to 1.2.

The term "degree of substitution" is understood within the framework of the present invention as the mean number of substituents per anhydroglucose unit of the starch. The degree of substitution can adopt values between 0 and 3.

A range of the average degree of substitution is preferably in the range from 0.2 to 0.5.

The starch propylphosphonate in accordance with the invention is preferably produced by conversion of polysaccharides, in particular of starch and preferably of depleted starch. In this respect, the polysaccharides, in particular the starch, preferably have a number average molar mass Mn in the range 3000 g/mol-5000 g/mol.

The starch propylphosphonate in accordance with the present invention is preferably made up of the repeating units

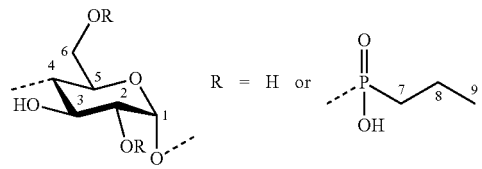

or contains these repeating units. Other substituents instead of R=H are also conceivable and covered by the invention.

The substitution with propylphosphonate is preferably possible at the positions 6, 2 and 3 of the glucose units, with positions 6 and 2 predominantly being substituted. It is furthermore possible to achieve a preferred substitution at position 6 or 2 by the choice of the reaction conditions. In the homogeneous reaction conditions reproduced in examples to 4, the substitution predominantly takes place at position 6. A preferred substitution at position 2 is possible by heterogeneous reaction conditions e.g. with NaOH.

The number of propylphosphonate units per anhydroglucose unit is the degree of substitution named within the framework of the present invention.

Starches of various sources (e.g. from potatoes, corn, manioc (tapioca), rice, peas, wheat and further types of grain) as well as specific starch types such as Hylon VII, amioca powder or waxy corn starch are conceivable as starting materials for the production of the starch propylphosphonate. The above list is an example and not exclusive.

Further details and advantages will be explained in more detail with reference to an embodiment shown in the drawing.

Figure 2:
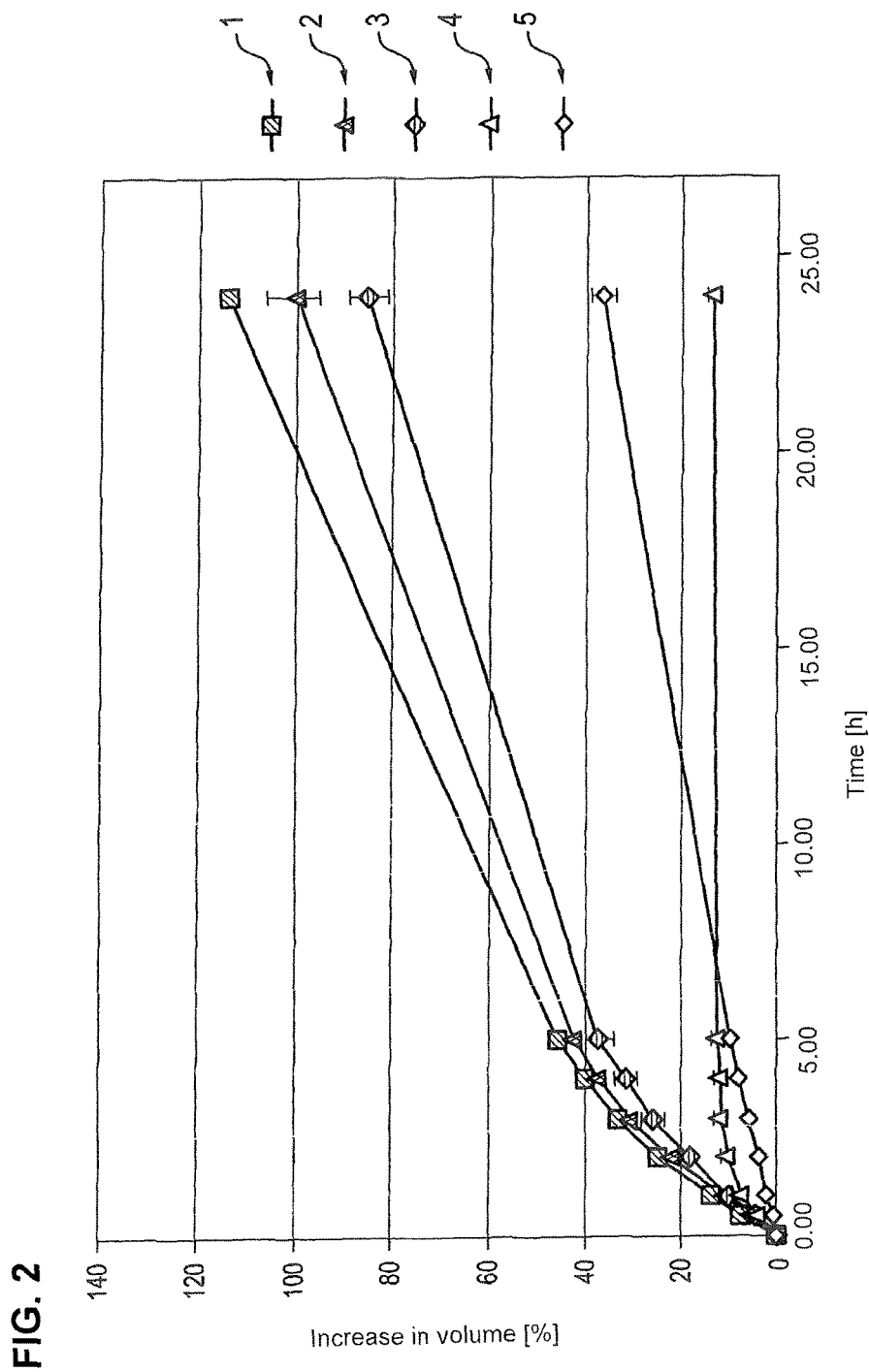
Figure 3:
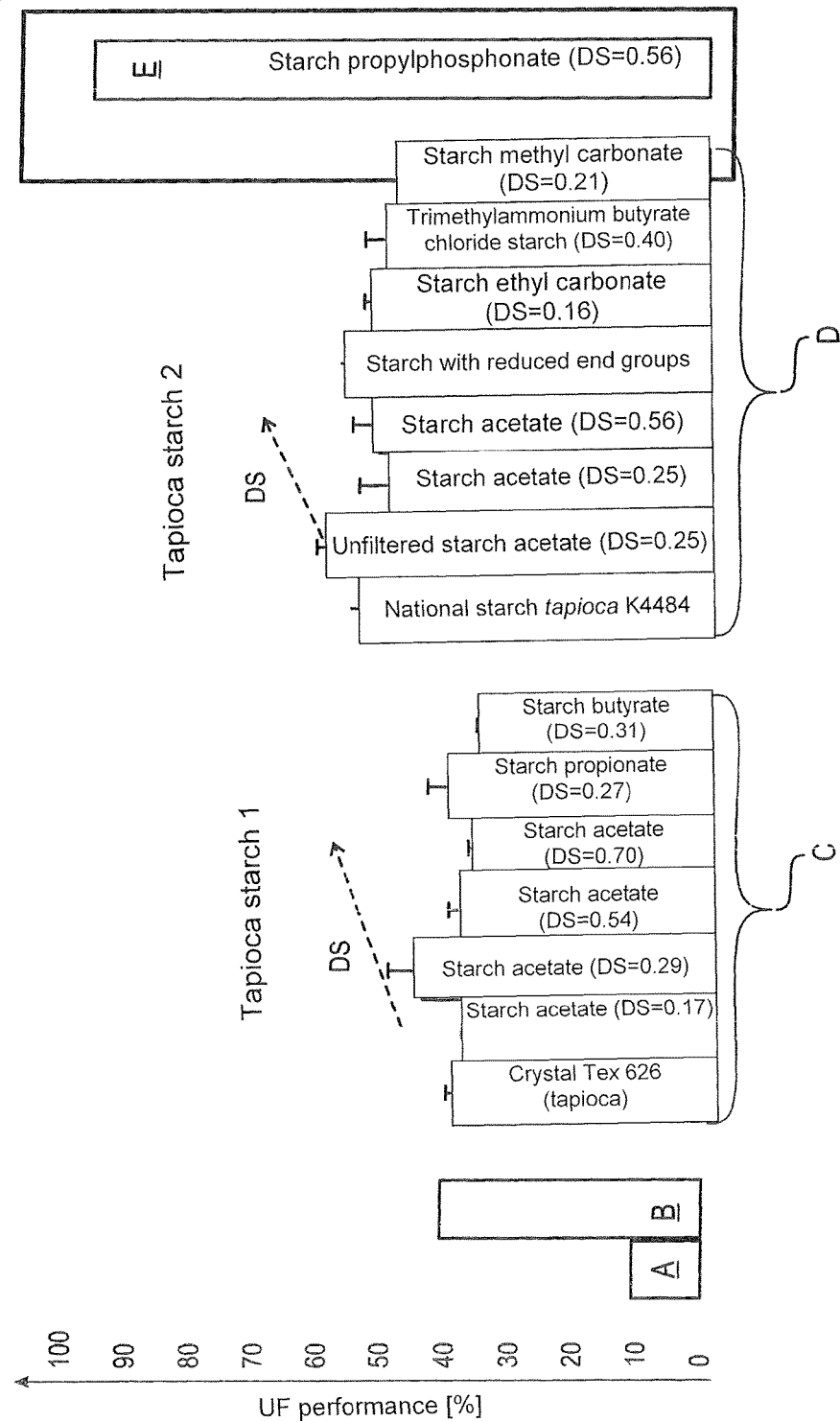

There are shown:

FIG. 1: schematic representations of a hose filled with the dialysis solution in accordance with the invention at different times;

FIG. 2: the increase in the volume of a hose filled with a dialysis solution for different osmotic agents over time;

FIG. 3: the volume increase of the hose after 24 hours dwell time for different osmotic agents; and FIGS. 4 to 11: $^1$H-NMR and $^{13}$C-NMR spectra of different starch propylphosphonates.

FIG. 1 shows a hose 10 whose wall is formed by a semipermeable membrane. The membrane can, for example, be cellulose or regenerated cellulose.

A dialysis solution L1 containing an osmotic agent is located in the interior of the hose 10. The hose 10 is located in a solution L2 which has the same composition as the solution L1 in the hose 10 with the sole difference that the solution L2 does not have any osmotic agent.

FIG. 1, left hand illustration, shows the arrangement at the time T=0, i.e. at the start of the experiment at which the filled hose 10 was placed into the solution L2.

FIG. 1, middle illustration, shows the arranged after a two-hour dwell time (T=2 h); and FIG. 1, right hand illustration shows the arrangement after a 24-hour dwell time (T=24 h).

As can be seen from a comparison of the illustrations of FIG. 1, water has flowed into the hose due to the osmotic effect of the solution L1 so that the volume of said hose increases accordingly over time.

FIG. 2 shows the volume increase in % (starting from the start of the experiment at T=0) over time for a further hose experiment for solutions having different osmotic agents. In this respect, the solutions 1, 2 and 3 have starch propylphosphonates having an average degree of substitution DS of 1.19 (solution 1), DS of 0.62 (solution 2) and DS of 0.23 (solution 3).

Reference numerals 4 and 5 relates to solutions with glucose (solution 4) and with icodextrin (solution 5).

The evaluation of the results for different osmotic agents is shown in FIG. 3, with FIG. 3 showing the volume increase, i.e. the UF performance (UF ultrafiltration) of the hose 10 after a 24-hour dwell time on the ordinate. The value 0% means that no volume change has resulted with respect to the start of the experiment (T=0); the value 100% means a doubling of the volume over the starting state at T=0.

The experiment conditions which form the basis for the results in accordance with FIG. 2 and FIG. 3 were identical for both FIGS. 2 and 3.

Reference symbol A shows the result for the use of glucose and illustrates the fact that a volume increase by 10% has taken place after a 24-hour dwell time. Reference symbol B shows the result for the use of an icodextrin solution which effects a volume increase of 40% after a 24-hour dwell time.

Reference symbol C marks solutions having different starches or starch derivatives derived from a tapioca starch having a number average molar mass of 4.898 g/mol (called "tapioca starch 1" in FIG. 3); and reference symbol D shows solutions having different starches and starch derivatives derived from a tapioca starch having a number average molar mass of 3.321 g/mol (called "tapioca starch 2" in FIG. 3). The starches used of groups C and D are each shown with increasing average degrees of substitution (DS) from left to right. The volume increase caused by the use of these osmotic agents is approximately in the range from 35% to 55%.

Reference numeral E shows a dialysis solution in accordance with the present invention which contains starch propylphosphonate, and indeed having an average degree of substitution (DS) of 0.54.

It becomes clear from FIG. 3 that on the use of the osmotic agents in accordance with the invention, i.e. on the use of starch propylphosphonates, a volume increase of more than 90% is achieved, i.e. a volume increase which is well above that which is reached with known osmotic agents.

The content (wt. %) of osmotic agents of all solutions shown in FIG. 3 as well as their other compositions is identical.

The experiment conditions for the results in accordance with FIGS. 2 and 3 are as follows:

A filling volume of 10 ml of a liquid was filled into a hose having a semipermeable hose wall of regenerated cellulose (MWCO: 1000 Da, Roth corporation). This liquid comprises an aqueous solution of an osmotic agent (starch propylphosphonate, glucose, icodextrin, starch or starch derivative) having a concentration of the osmotic agent of 5 wt. %, with further ingredients being present by $Ca^{2+}$ in a concentration of 1 mmol/l, $Mg^{2+}$ in a concentration of 0.5 mmol/l, $Na^+$ in a concentration of 138 mmol/l, $Cl^-$ in a concentration of 106 mmol/l and lactate in a concentration of 35 mmol/l.

This filled hose was stored while being moved at a temperature of 38° C. in a bath of the same experiment solution, but without an osmotic agent, for 24 hours.

The volume increase of the filling volume of the hose reflecting the osmotic effect of the agent was determined at different times. As can be seen from FIG. 2, the osmotic agents in accordance with the present invention were compared with known osmotic agents in the form of glucose and icodextrin.

FIG. 2 shows that the volume increase of the hose for all dialysis solutions containing starch propylphosphonate is above 80% after a 24-hour dwell time. A volume increase of approximately 115% after 24 hours was achieved as the maximum value.

In contrast, the final values after 24 h for icodextrin were at approximately 35% and those of glucose at approximately 13%.

The osmotic agents in accordance with the invention not only show an increased ultrafiltration efficiency after 24 hours, but also a higher value with small dwell times with respect to icodextrin.

While the volume increase with icodextrin has a substantially linear progression, a comparatively steep increase can be seen with the dialysis solutions containing starch propylphosphonates, said steep increase bottoming out at higher dwell times and merging into a substantially linear progression.

The increase of the hose volume at low dwell times on the use of starch propylphosphonates is comparable with that of glucose. At higher values, however, the volume increase with glucose as the osmotic agent is much smaller and remains constant after a dwell time of approximately three hours, as can be seen from FIG. 2.

The starch propylphosphonates in accordance with solutions 1, 2 and 3 were produced from tapioca starch having a number average molar mass of 3.321 g/mol.

Embodiments for the production of starch propylphosphonate will be described in the following. With the exception of the respectively named differences, the production conditions for all four examples shown below were identical.

EXAMPLE 1

40.0 g depleted tapioca starch (Mn=3.321 g/mol) are suspended in 360 ml N,N-dimethylformamide (DMF) and treated in a nitrogen atmosphere while stirring at 120° C. for 2 h. After cooling to 80° C., 14 g LiCl are added and the starch dissolves with further stirring after approximately 1 h.

The solution is heated to 100° C. and 23.6 g (0.3 mol/mol anhydroglucose unit, AGU) propylphosphonic acid anhydride (T3P) is added in DMF (51.5% w/w). After 3 h reaction time, the product is precipitated into 3 l ethanol, filtered, washed three times with 1 l ethanol and reprecipitated from 70 ml water in 1 l ethanol.

Figure 4:
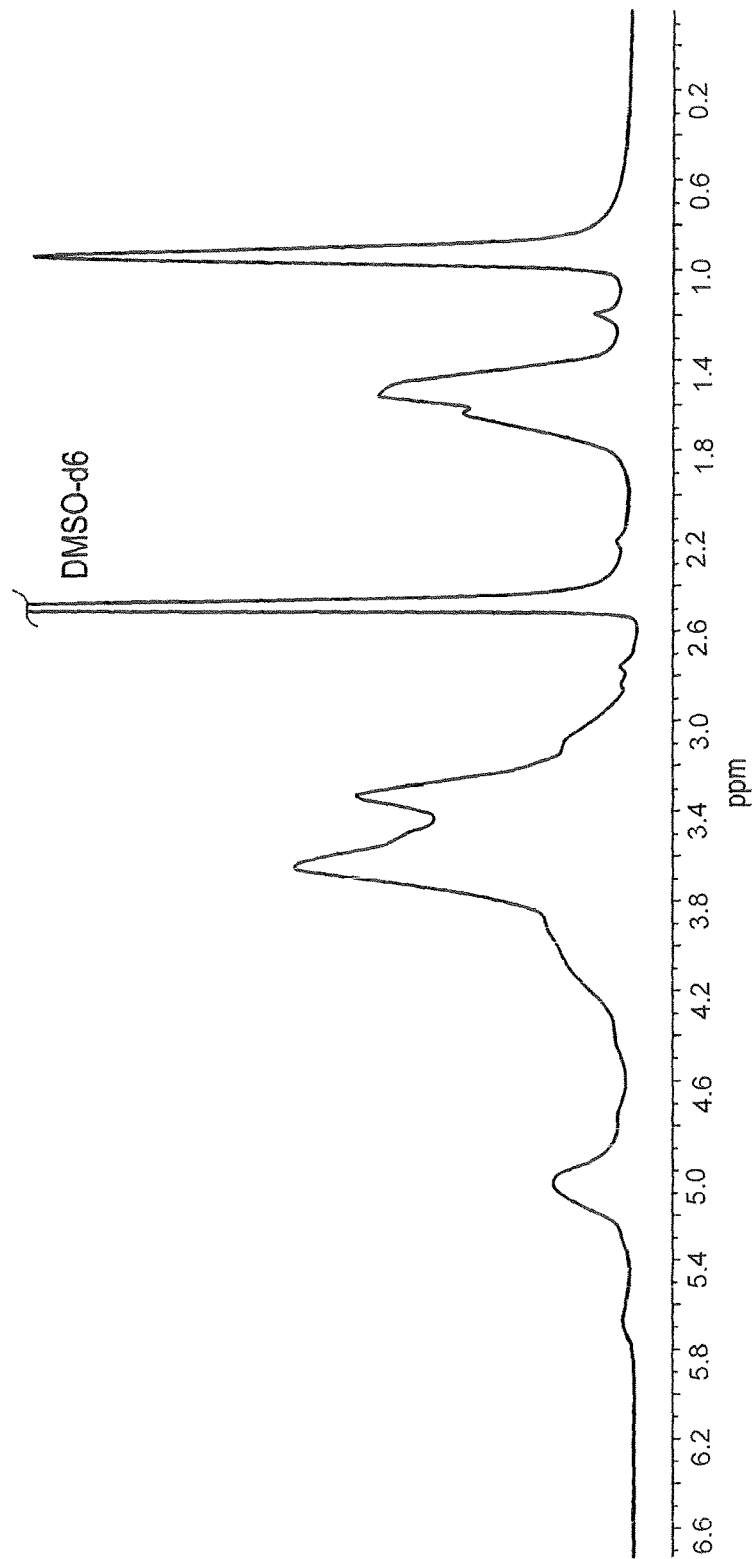
Figure 5:
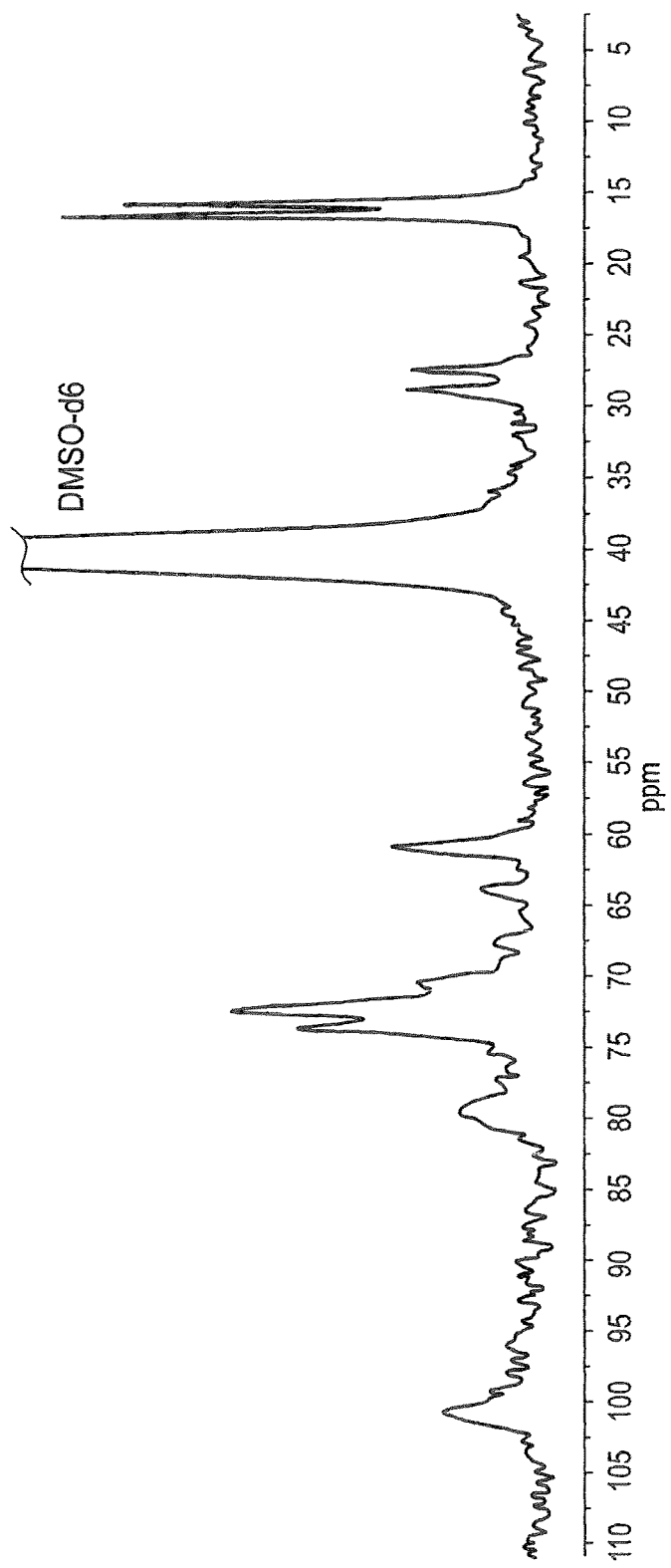

The product is dissolved in 400 ml water, the solution is treated with Amberlite IR120 ($H^+$ form), the ion exchanger is separated and the polymer solution is freeze-dried. The structural proof took place by $^1H$ and $^{13}C$ NMR spectra (FIGS. 4 and 5).

Average degree of substitution DS (determined by means of $^1H$ NMR spectroscopy): 0.54.

EXAMPLE 2

Figure 6:
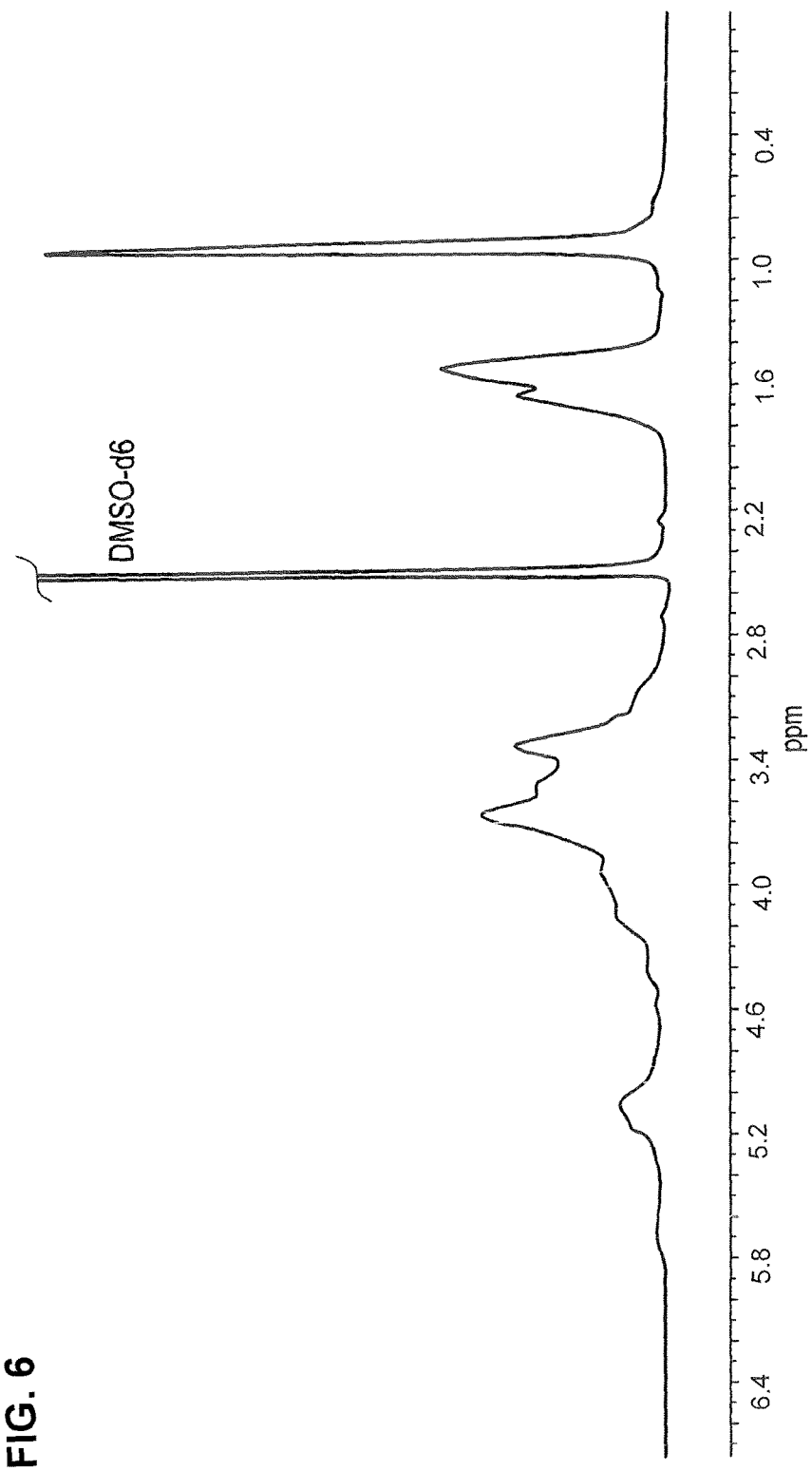
Figure 7:
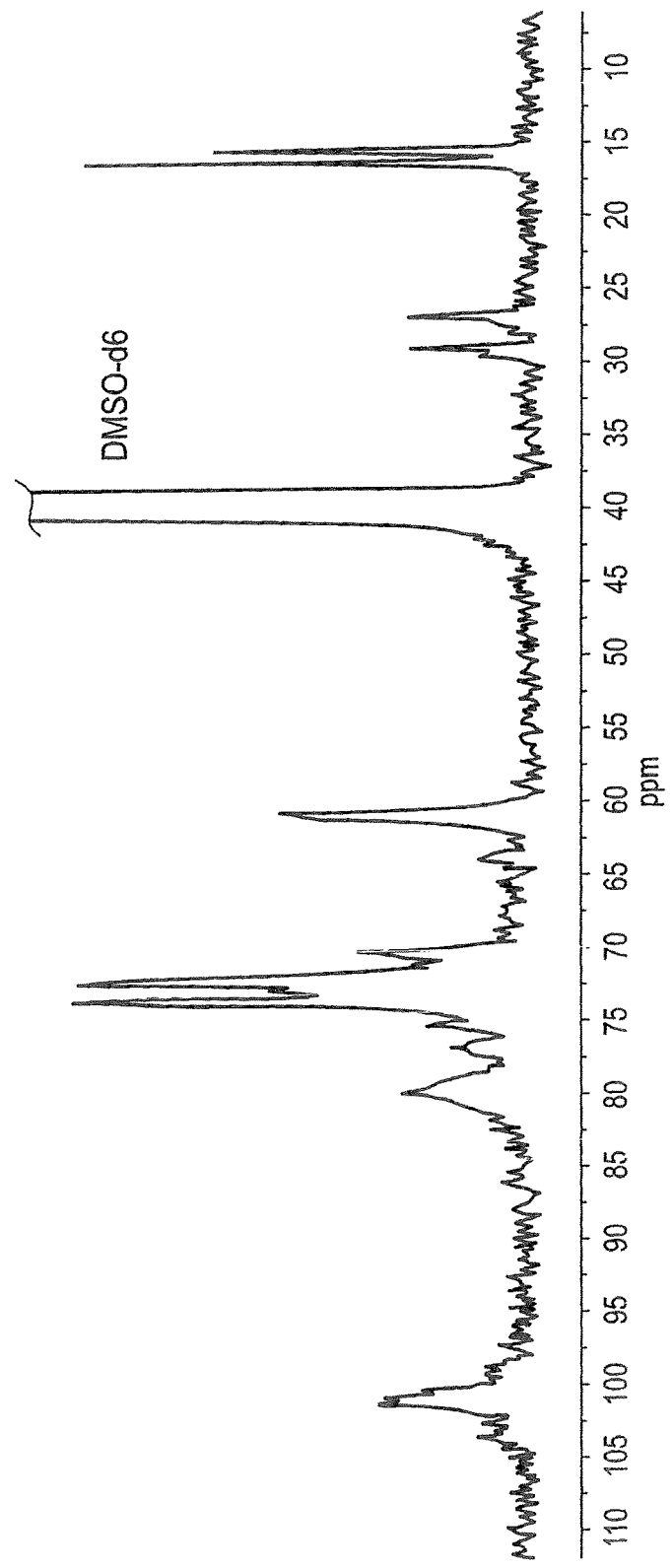

In accordance with Example 1, depleted tapioca starch having a molar mass (Mn) of 4.898 g/mol is converted under identical conditions to Example 1. The precipitation and reprecipitation from an aqueous solution take place using acetone. $^1H$ and $^{13}C$ NMR spectra confirm the structure (FIGS. 6 and 7).

DS (determined by means of $^1H$ NMR spectroscopy): 0.70

EXAMPLE 3

Figure 8:
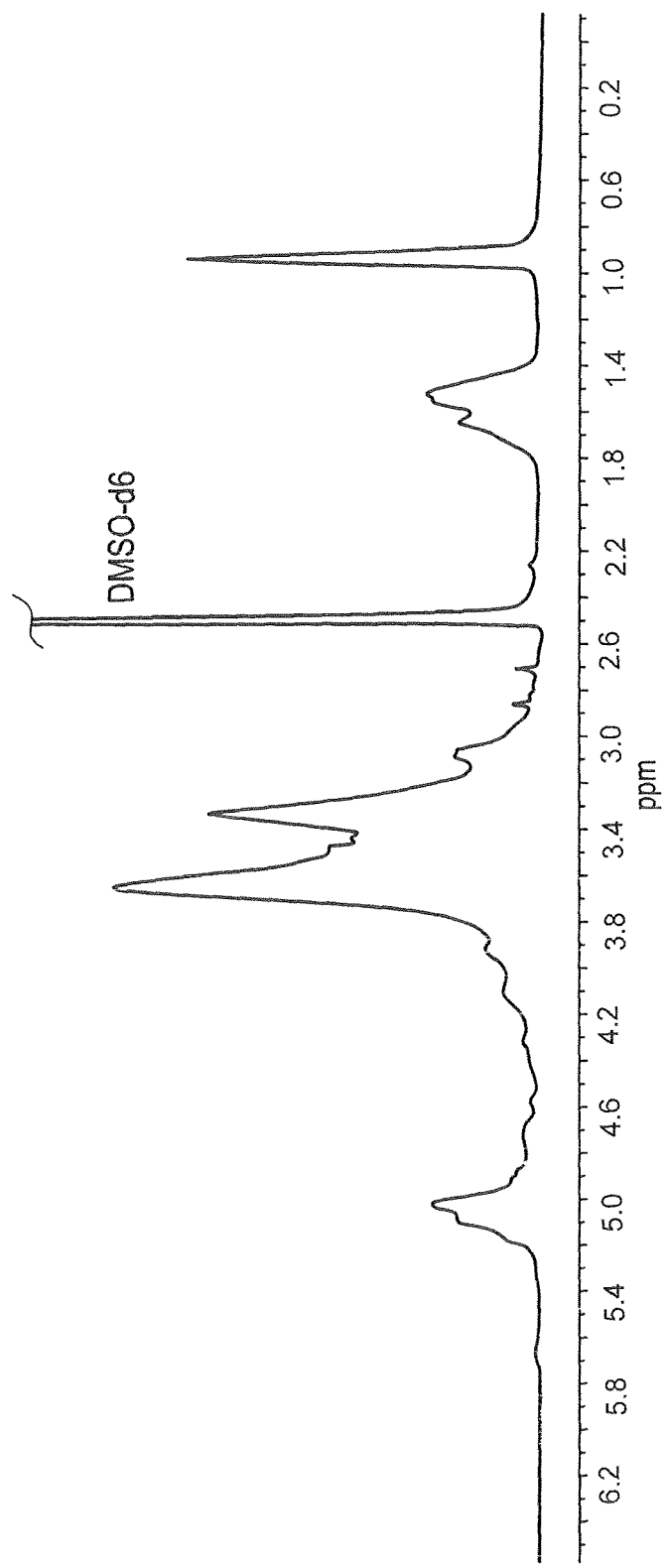
Figure 9:
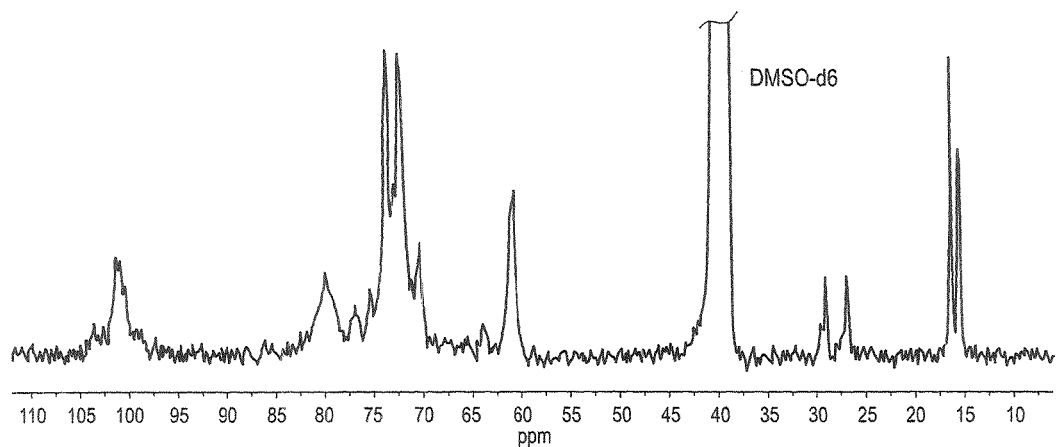

In accordance with Example 1, 40.0 g of depleted tapioca starch is converted (Mn=3.321 g/mol) with 7.9 g (0.1 mol/mol AGU) T3P in DMF (50%. w/w). The starch derivative is isolated and purified by precipitation and reprecipitation with isopropanol. $^1H$ and $^{13}C$ NMR spectra confirm the structure (FIGS. 8 and 9).

DS (determined by means of $^1H$ NMR spectroscopy): 0.23

EXAMPLE 4

Figure 10:
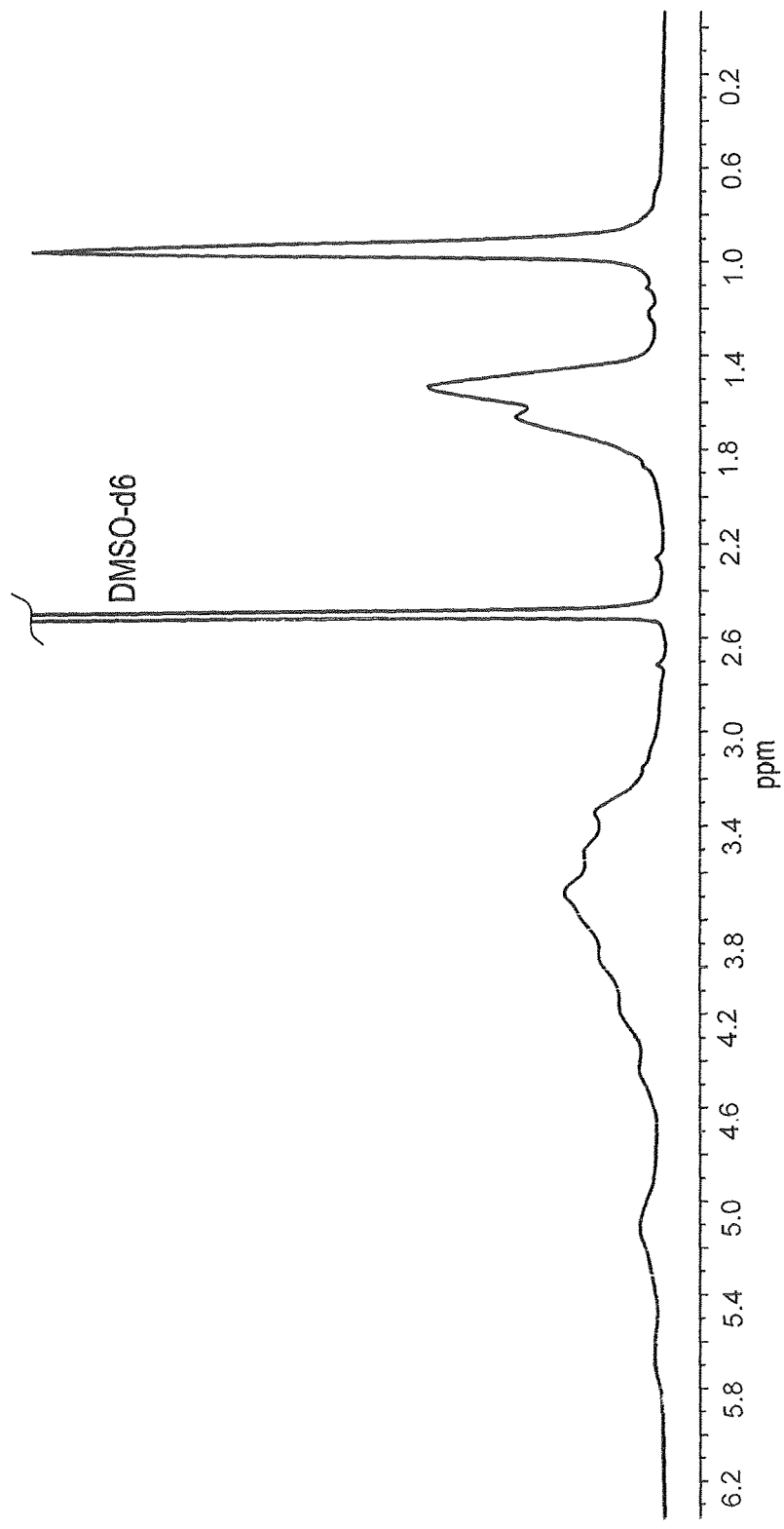
Figure 11:
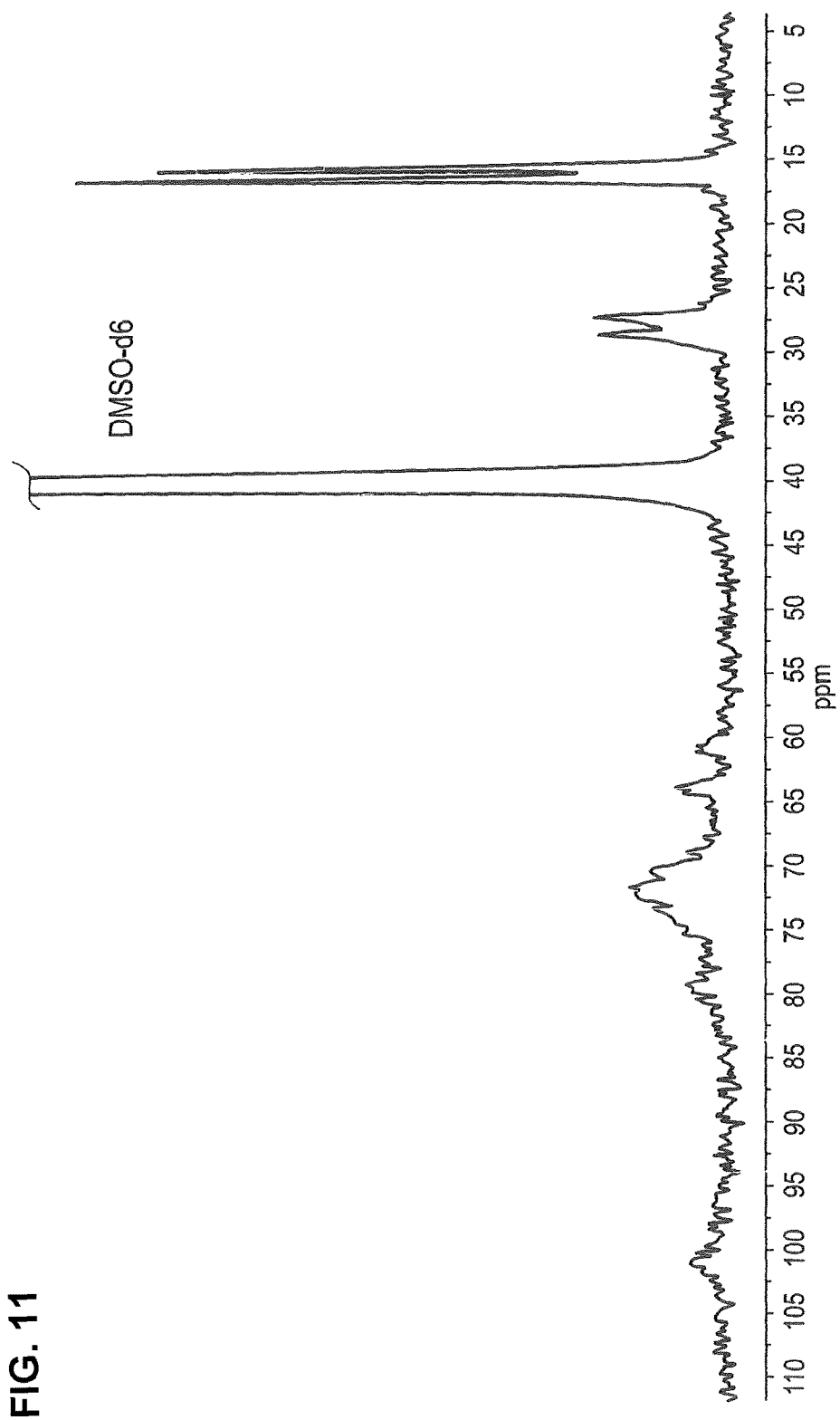

In accordance with Example 1, 40.0 g of depleted tapioca starch is converted (Mn=3.321 g/mol) with 47.1 g (0.6 mol/mol AGU) T3P in DMF (50%. w/w). The starch derivative is isolated and purified by precipitation and reprecipitation with isopropanol. $^1H$ and $^{13}C$ NMR spectra confirm the structure (FIGS. 10 and 11). DS (determined by means of $^1H$ NMR spectroscopy): 1.19

A dialysis solution is provided by the present invention which has a substantially increased osmotic activity with respect to known dialysis solutions, which is due to the use of starch propylphosphonate as the osmotic agent.

The dialysis solution is thus suitable, for example, as a peritoneal dialysis solution or also within the framework of hemodialysis, hemodiafiltration or also within the framework of other blood treatment processes in which a treatment solution in the form of the dialysis solution in accordance with the invention is used.

The invention claimed is:

1. A dialysis solution having at least one osmotic agent, characterized in that the osmotic agent is starch propylphosphonate produced from starch having a number average molecular weight in the range from 3000 g/mol to 5000 g/mol.

2. A dialysis solution in accordance with claim 1, characterized in that the dialysis solution contains exactly one kind of starch propylphosphonate or a plurality of kinds of starch propylphosphonates.

3. A dialysis solution in accordance with claim 1, characterized in that the dialysis solution does not contain any further osmotic agent except for starch propylphosphonate.

4. A dialysis solution in accordance with claim 1, characterized in that the starch propylphosphonate is completely water-soluble.

5. A dialysis solution in accordance with claim 1, characterized in that the starch propylphosphonate has an average degree of substitution in the range from 0.1 to 1.2.

6. A dialysis solution in accordance with claim 5, characterized in that the starch propylphosphonate has an average degree of substitution in the range from 0.2 to 0.5.

7. A dialysis solution in accordance with claim 1, characterized in that the solution comprises electrolytes and a buffer.

8. A dialysis solution in accordance with claim 7, characterized in that the electrolytes comprise the ions of sodium and/or potassium and/or calcium and/or magnesium.

9. A dialysis solution in accordance with claim 7, characterized in that the buffer comprises lactate ions and/or hydrogen carbonate ions.

10. A method for dialysis, comprising utilizing the dialysis solution in accordance with claim 1 for the dialysis.

11. The method in accordance with claim 10, characterized in that the dialysis is hemodialysis or hemodiafiltration.

12. A method in accordance with claim 10, characterized in that the dialysis is peritoneal dialysis.

13. A chemical compound consisting of or comprising one or more water-soluble starch propylphosphonates.

14. A chemical compound in accordance with claim 13, characterized in that
the starch propylphosphonate has an average degree of substitution in the range from 0.1 to 1.2.

15. The chemical compound of claim 13, wherein said chemical compound consists of one or more starch propylphosphonates.

\* \* \* \* \*